US006692458B2

(12) United States Patent
Forman et al.

(10) Patent No.: US 6,692,458 B2
(45) Date of Patent: Feb. 17, 2004

(54) INTRA-PERICARDIAL DRUG DELIVERY DEVICE WITH MULTIPLE BALLOONS AND METHOD FOR ANGIOGENESIS

(75) Inventors: Michael Robert Forman, Vadnais Heights, MN (US); Donald E. Bobo, Jr., Santa Ana, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 0 days.

(21) Appl. No.: 09/741,544

(22) Filed: Dec. 19, 2000

(65) Prior Publication Data

US 2003/0036726 A1 Feb. 20, 2003

(51) Int. Cl.[7] .............................................. A61M 31/00
(52) U.S. Cl. .............................. 604/93.01; 604/101.03; 604/264; 604/528; 604/919; 606/192
(58) Field of Search .......................... 604/93.01, 96.01, 604/101.02, 101.03, 101.04, 264, 523, 528, 915, 917, 919; 606/192, 194

(56) References Cited

U.S. PATENT DOCUMENTS

| | | | |
|---|---|---|---|
| 4,531,936 A | | 7/1985 | Gordon |
| 4,824,436 A | | 4/1989 | Wolinsky |
| 4,911,163 A | * | 3/1990 | Fina .......................... 606/127 |
| 4,968,306 A | | 11/1990 | Huss et al. |

(List continued on next page.)

FOREIGN PATENT DOCUMENTS

| | | |
|---|---|---|
| WO | WO 9716169 | 5/1997 |
| WO | WO 9824378 | 6/1998 |
| WO | WO 9913785 | 3/1999 |
| WO | WO 9913936 | 3/1999 |

OTHER PUBLICATIONS

Waxman et al.; Persistent Primary Coronary Dilation Induced by Transatrial Delivery of Nitroglycerin Into the Pericardial Space: A Novel Approach for Local Cardiac Drug Delivery; Journal of the American College of Cardiology; vol. 33 No. 7, Jun. 1999:2073–7.

Laham et al.; Therapeutic Myocardial Angiogenesis Using Percutaneous Intrapericardial Drug Delivery; Clin. Cardiol. vol. 22 (Suppl I) I–6–I–99 (1999).

*Primary Examiner*—Charles G. Freay
*Assistant Examiner*—John F Belena
(74) *Attorney, Agent, or Firm*—Stradling Yocca Carlson & Rauth; Debra D. Condino

(57) ABSTRACT

A catheter and a method for using the catheter for site specific delivery of agents to or collecting agents from biological spaces. The catheter includes an inner shaft longitudinally movable within an outer shaft, each shaft having at least one balloon and at least one lumen formed therein. The catheter prevents leaking through a biological membrane by sealing the catheter tip passageway through the biological membrane with inflatable balloons on either side of the biological membrane. Further, the inflated balloons secure the position of the catheter relative to the biological membrane and the biological space targeted for therapy or diagnosis.

56 Claims, 9 Drawing Sheets

U.S. PATENT DOCUMENTS

| | | |
|---|---|---|
| 5,071,428 A | 12/1991 | Chin et al. |
| 5,087,244 A | 2/1992 | Wolinsky et al. |
| 5,112,305 A | 5/1992 | Barath et al. |
| 5,167,628 A | 12/1992 | Boyles |
| 5,176,643 A | 1/1993 | Kramer et al. |
| 5,192,290 A * | 3/1993 | Hilal .......................... 606/159 |
| 5,254,089 A | 10/1993 | Wang |
| 5,269,326 A * | 12/1993 | Verrier ...................... 128/642 |
| 5,279,565 A | 1/1994 | Klein et al. |
| 5,304,121 A | 4/1994 | Sahatjian |
| 5,306,250 A | 4/1994 | March et al. |
| 5,368,566 A | 11/1994 | Crocker |
| 5,397,307 A | 3/1995 | Goodin |
| 5,415,636 A | 5/1995 | Forman |
| 5,458,568 A | 10/1995 | Racchini et al. |
| 5,458,573 A | 10/1995 | Summers |
| 5,464,395 A | 11/1995 | Faxon et al. |
| 5,514,092 A | 5/1996 | Forman et al. |
| 5,523,092 A | 6/1996 | Hanson et al. |
| 5,527,292 A | 6/1996 | Adams et al. |
| 5,538,504 A | 7/1996 | Linden et al. |
| 5,538,512 A | 7/1996 | Zenzon et al. |
| 5,554,114 A | 9/1996 | Wallace et al. |
| 5,554,119 A | 9/1996 | Harrison et al. |
| 5,558,642 A | 9/1996 | Schweich, Jr. et al. |
| 5,569,184 A | 10/1996 | Crocker et al. |
| 5,569,215 A | 10/1996 | Crocker |
| 5,571,086 A | 11/1996 | Kaplan et al. |
| 5,599,306 A | 2/1997 | Klein et al. |
| 5,609,574 A | 3/1997 | Kaplan et al. |
| 5,626,562 A | 5/1997 | Castro |
| 5,634,895 A | 6/1997 | Igo et al. |
| 5,652,225 A | 7/1997 | Isner |
| 5,674,192 A | 10/1997 | Sahatjian et al. |
| 5,681,278 A | 10/1997 | Igo et al. |
| 5,693,029 A | 12/1997 | Leonhardt |
| 5,698,531 A | 12/1997 | Nabel et al. |
| 5,709,874 A | 1/1998 | Hanson et al. |
| 5,713,860 A | 2/1998 | Kaplan et al. |
| 5,716,340 A | 2/1998 | Schweich, Jr. et al. |
| 5,733,267 A * | 3/1998 | Del Toro .................... 604/280 |
| 5,772,632 A * | 6/1998 | Forman ...................... 604/101 |
| 5,795,318 A | 8/1998 | Wang et al. |
| 5,797,870 A | 8/1998 | March et al. |
| 5,817,144 A | 10/1998 | Gregory |
| 5,827,216 A | 10/1998 | Igo et al. |
| 5,833,658 A | 11/1998 | Levy et al. |
| 5,836,905 A | 11/1998 | Lemelson et al. |
| 5,836,967 A | 11/1998 | Schneider |
| 5,843,051 A | 12/1998 | Adams et al. |
| 5,855,563 A | 1/1999 | Kaplan et al. |
| 5,865,794 A | 2/1999 | Castro |
| 5,873,865 A | 2/1999 | Horzewski et al. |
| 5,876,373 A | 3/1999 | Giba et al. |
| 5,882,334 A | 3/1999 | Sepetka et al. |
| 5,925,016 A | 7/1999 | Chornenky et al. |
| 6,071,263 A | 6/2000 | Kirkman |
| 6,117,153 A * | 9/2000 | Lary et al. .................. 606/170 |
| 6,129,704 A | 10/2000 | Forman et al. |
| 6,408,203 B2 * | 6/2002 | Mackin ....................... 600/433 |
| 6,447,539 B1 * | 9/2002 | Nelson et al. ............. 623/1.11 |
| 6,458,092 B1 * | 10/2002 | Gambale et al. .............. 604/22 |
| 2001/0007937 A1 | 7/2001 | MacKin |

* cited by examiner

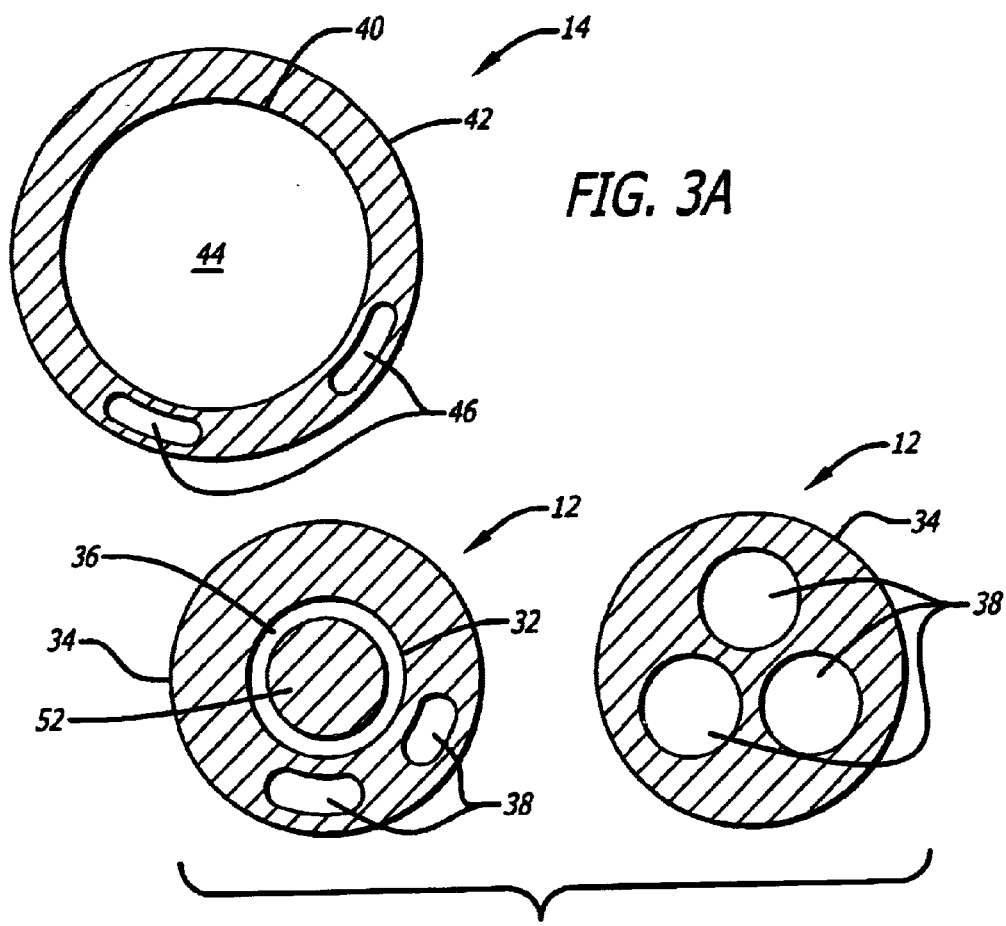
FIG. 3A
FIG. 3B
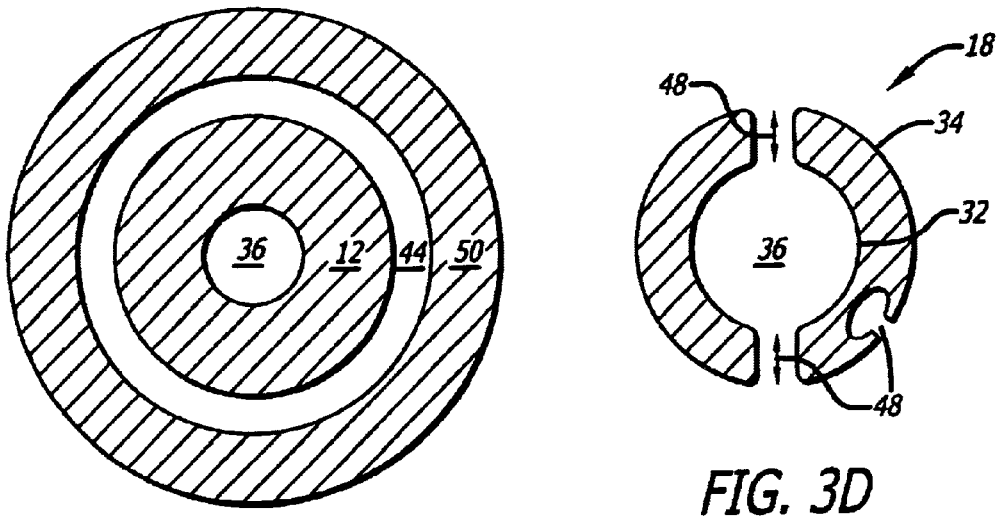
FIG. 3C
FIG. 3D

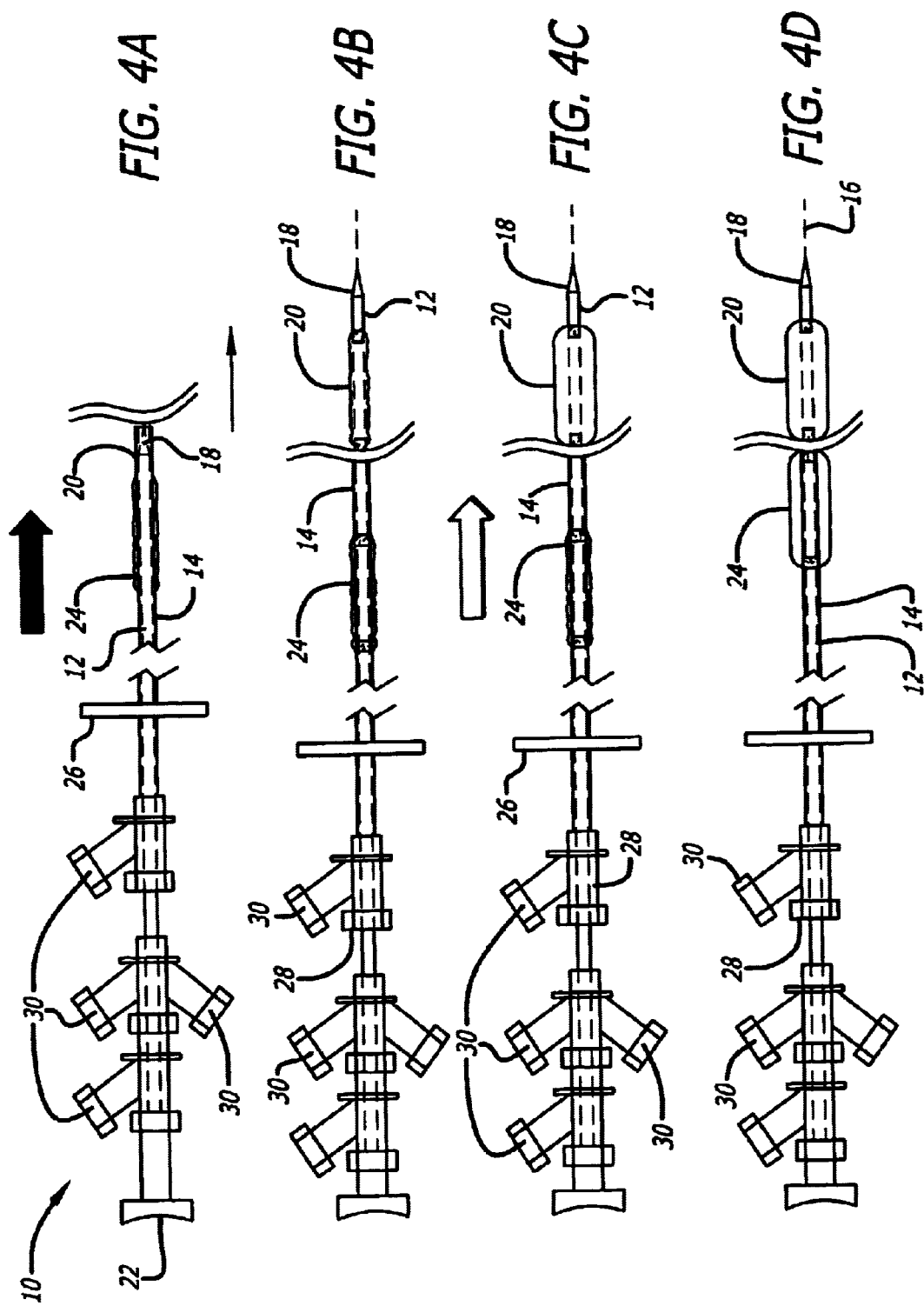

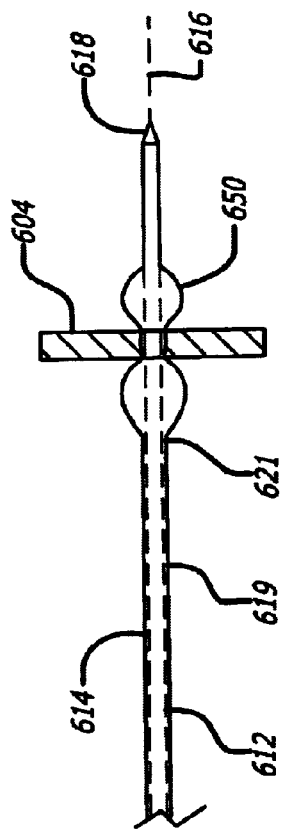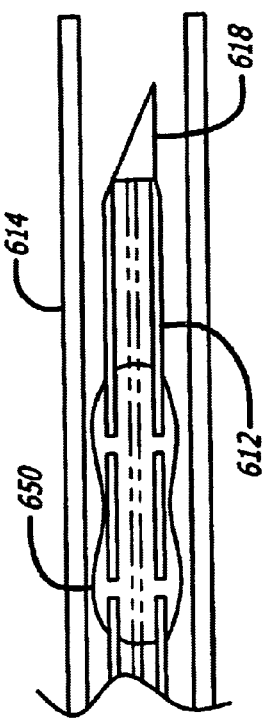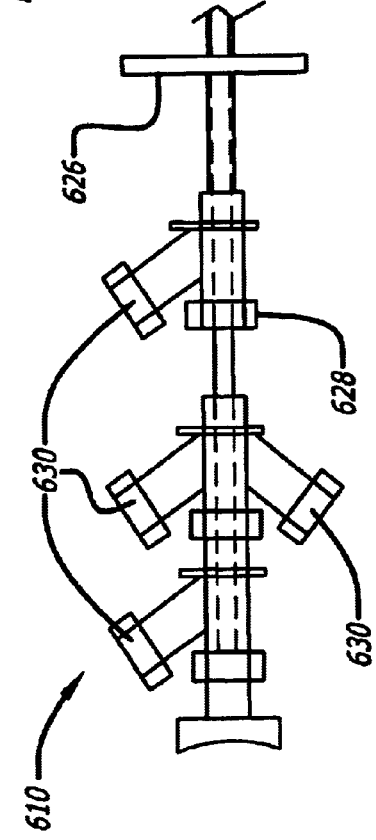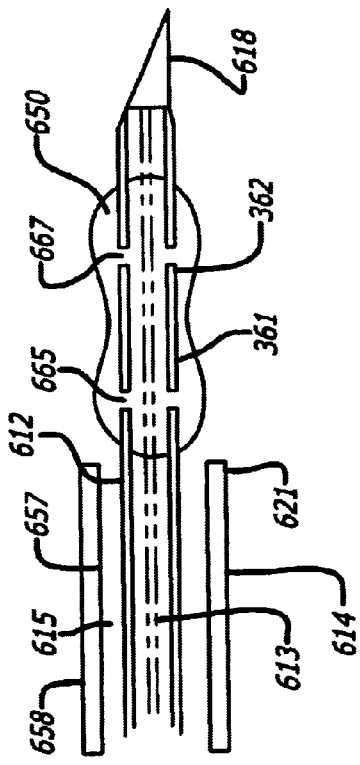
FIG. 6A
FIG. 6B
FIG. 6C

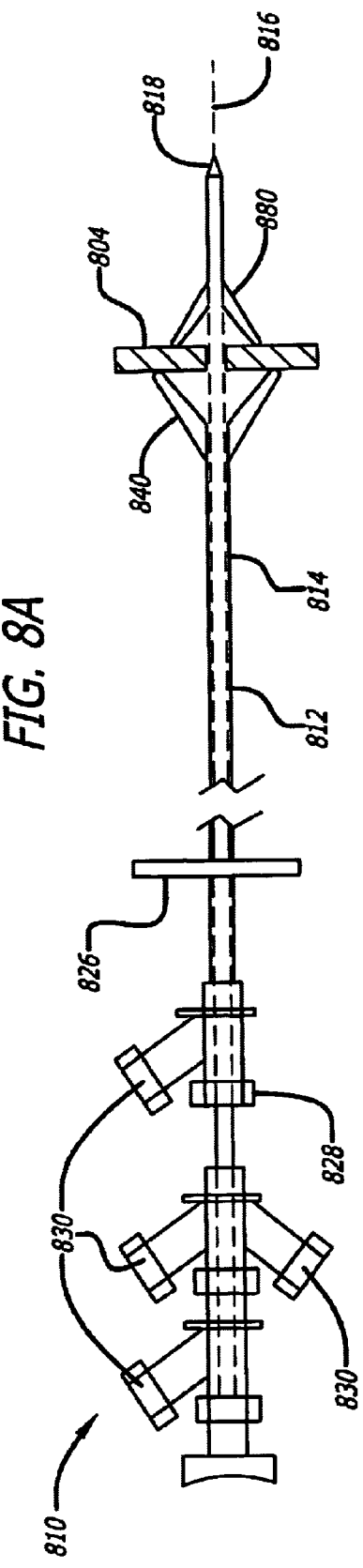
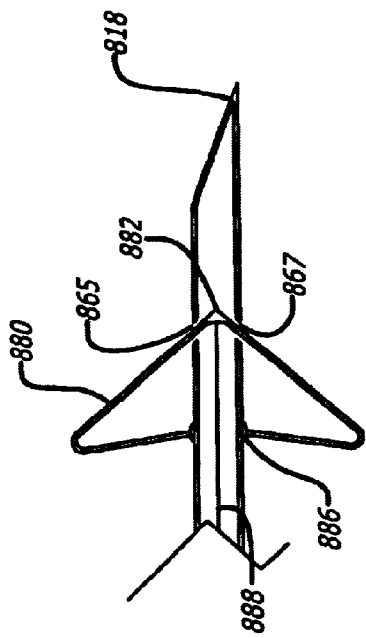
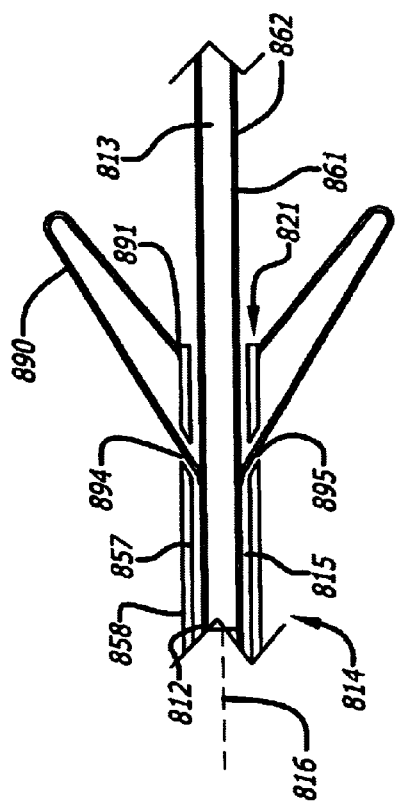

INTRA-PERICARDIAL DRUG DELIVERY DEVICE WITH MULTIPLE BALLOONS AND METHOD FOR ANGIOGENESIS

BACKGROUND OF THE INVENTION

This invention relates generally to a catheter device and methods for the site-specific delivery of agents to biological spaces in medical procedures. More particularly, the invention relates to a catheter device utilizing multiple balloons and a method of site-specific delivery of agents into the pericardial space for treatment of the heart.

Heart disease is the leading cause of death in the United States. One form of heart disease is caused by the formation of sclerotic plaques within blood vessels. These pathways prevent blood from flowing freely though vessels to the tissues the vessels supply. The most dangerous plaques are those which form in the coronary arteries, preventing the flow of oxygenated blood through the coronary arteries to the heart.

There are generally two surgical procedures for treating heart disease. One procedure involves methods to increase blood supply to the effected areas of the heart by clearing sclerotic plaques from the existing vessels. In angioplasty, for example, a small dilating balloon is inserted into the vessel to open the vessel to increase blood flow. A second procedure involves providing new pathways for blood flow. New pathways can be created by grafting in vessels (coronary artery bypass surgery) or by inducing the growth and development of new collateral vessels (therapeutic angiogenesis).

The induction of new collateral vessels can be achieved by injections of angiogenic agents directly into the heart tissue, into vessels (coronary arteries), or into the space surrounding the heart (pericardium). Direct injections of agents into the heart muscle or vessels can result in tissue injury, scarring and rapid washout of the agent into the peripheral circulatory system. Furthermore, these direct injections require surgical procedures which are more costly and require a longer recovery period than catheter based procedures. Thus, direct injections are not preferable. However, indirect injections into the pericardium avoid these difficulties.

The pericardium is a membrane that surrounds the heart and isolates it from the remainder of the body. The small space between the heart and the pericardium is the pericardial space, which is filled with pericardial fluid. The pericardial fluid is in constant contact with the heart muscle and coronary arteries and provides a relatively large reservoir for sustained release of drugs compared to intra-coronary methods or direct injection. Introduction of an agent to the pericardial space allows the agent to be contained in an area localized around the heart (epicardium and epicardial vessels). This is beneficial in the following ways: 1) a lower dose of drug can be used than if given systemically due to the low volume of the pericardial fluid, 2) the low rate of turn over of the pericardial fluid allows high concentration of the agent to be maintained over a longer period, and 3) it keeps the agents out of systemic circulation where the agent may cause adverse side effects.

However, the pericardial space is shallow, and thus difficult to access without puncturing (and damaging) the underlying heart tissue or coronary arteries. Previous attempts to access the pericardial space have utilized a syringe and needle combination, such as is used in pericardiocentesis, to directly inject agents into the pericardial space via the patient's chest. One of the risks inherent in such devices is the tendency for the needle to go beyond the pericardial space and to pierce the heart muscle. Some devices have utilized suction to draw the pericardial tissue towards the needle and thereby limit the distance the needle has to travel to deliver fluid to the pericardial space.

One attempt to overcome some of the limitations inherent in procedures done through the patient's chest is a catheter based system disclosed in U.S. Pat. No. 5,269,326 to Verrier, which has been incorporated by reference in its entirety. Verrier discloses the use of a catheter to approach the pericardial space via the right auricle, transvenously. The device takes advantage of the fact that the right auricle lies tangential to and between the pericardium and epicardium such that the catheter steered into the right auricle will be positioned substantially parallel with the wall of the pericardium. This approach minimizes the risk of damage to the pericardium or epicardium. However, using a catheter to pierce the pericardial wall can result in pericardial fluid flowing back into the atrium, blood flowing from the atrium into the pericardial space, and the therapeutic agent could end up being systemically administered.

Another approach to introducing medicaments directly into the pericardium is disclosed in U.S. Pat. No. 5,797,870 to March et al., which has been incorporated by reference in its entirety. March et al. discloses delivering a gene therapy agent into the pericardial sac either surgically or by transvascular means. In the catheter based embodiment the distal end of the catheter comprises a hypotube configured as a helical coil which is to be screwed into a heart wall to access the pericardial space. Like the device and method disclosed in Verrier, the device and method of March et al. is also susceptible to the backflow of pericardial fluid into the atrium and the ultimate systemic administration of the therapeutic agent.

What is needed, and what is provided by the present invention, is a catheter based device and method that accesses the pericardial space through the right auricle but is capable of sealing the access site so that the therapeutic agent is locally administered and flow between the auricle and the pericardial space is minimized.

BRIEF SUMMARY OF THE INVENTION

The present invention provides an improved agent delivery catheter which obviates, for practical purposes, the above mentioned limitations.

One feature of the invention is a device for accessing the pericardial space while minimizing the risk of injury to the heart during the pericardial catheterization.

Another feature of the invention is a catheter device which minimizes leakage from the pericardium and bleeding from the atrium into the pericardial space during catheterization of a defined biological space, such as the pericardial space.

Another feature of the invention is to provide a catheter device which minimizes longitudinal movement of the catheter from a site-specific location during the delivery or collection of agents from a defined biological space, such as the pericardial space.

Another feature of the invention is a device having a lumen which communicates with the pericardial fluid for the site specific introduction of agents into or collection of fluid from the pericardial space.

In accordance with one aspect of the present invention, the catheter includes an inner shaft longitudinally movable within an outer shaft, wherein each shaft has at least one lumen within it and at least one balloon attached to it.

In accordance with an additional embodiment of the present invention, the catheter includes an inner shaft longitudinally movable within an outer shaft, wherein inner shaft has at least one lumen within it and at least one balloon attached to it.

In accordance with an additional embodiment of the present invention, the catheter includes an inner shaft longitudinally movable within an outer shaft, wherein each shaft has at least one lumen within it and at least two deployable wire supports attached thereto and includes at least one balloon attached therebetween.

The catheter may include at least one lumen in each shaft, wherein the lumen may contain a guidewire, a wire support deployment mechanism, a balloon inflation source, or an agent delivery or collection source.

The catheter may include marker bands on each shaft, such that the marker bands can be used to detect the position of the shafts relative to one another or relative to the pericardial space.

The inner shaft of the catheter may include a distal tip to penetrate the surface membrane of the biological space. The tip may further be radio-opaque so that its position can be detected during use.

The above described and many other features and attendant advantages of the present invention will become apparent from a consideration of the following detailed description when considered in conjunction with the accompanying drawings.

BRIEF DESCRIPTION OF THE DRAWINGS

A detailed description of the embodiments of the invention will be made with reference to the accompanying drawings, wherein like numerals designate corresponding parts in the several figures.

FIGS. 3A–3D are a cross sectional views of the A) outer shaft; B) inner shaft; C) inner shaft within the outer shaft; and D) the present invention within a guide catheter;

FIGS. 4A–4D are side views of an exemplary embodiment of the present invention in various stages of application;

FIGS. 6A–6C are side views of A) another exemplary embodiment of the present invention; B) the distal portion of the embodiment with the inner shaft deployed beyond the outer shaft C) the inner shaft non-deployed within the outer shaft;

FIGS. 8A–8C are side views of A) another exemplary embodiment of the present invention; B) the distal portion of the outer shaft of the present invention; C) the inner shaft extended beyond the outer shaft.

DETAILED DESCRIPTION OF THE INVENTION

Disclosed herein is a detailed description of various illustrated embodiments of the invention. This description is not to be taken in a limiting sense, but is made merely for the purpose of illustrating the general principles of the invention. The section titles and overall organization of the present detailed description are for the purpose of convenience only and are not intended to limit the present invention.

Figure 1:
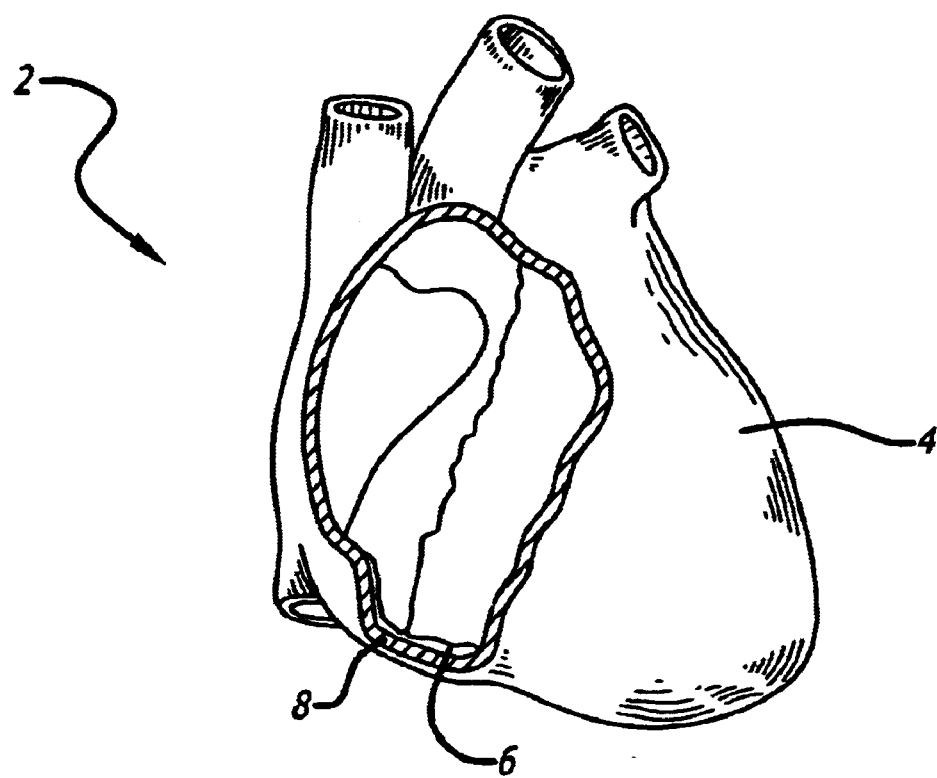
FIG. 1 is a diagrammatic representation of the heart.

FIG. 1 illustrates the heart 2 generally. The pericardium, or pericardial sac or membrane 4, surrounds the heart 2 (epicardium, myocardium and endocardium). A portion of the pericardium has been cut away to show the underlying heart, and the small space between the heart and the pericardium is the pericardial space 6. The cut edge of the pericardium is 8. The pericardial space 6 is one example of a defined biological space site-specifically targeted for the delivery or collection of agents by catheterization.

Detailed Description of the First Embodiment

Figure 2:
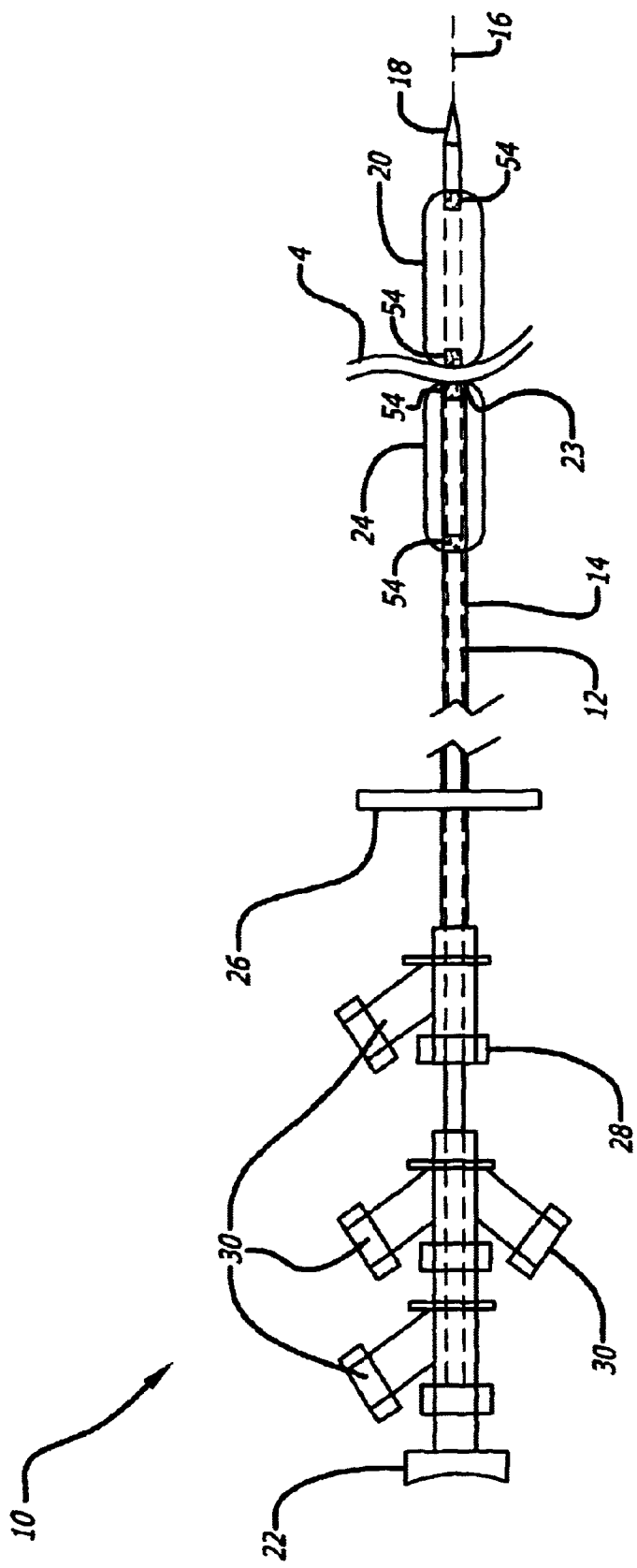
FIG. 2 is a side view of an exemplary embodiment of the present invention.

As illustrated in FIG. 2, one embodiment of the catheter 10, generally comprises an inner shaft 12 longitudinally movable within an outer shaft 14 along the catheter longitudinal axis 16. The inner shaft 12 has at its most distal end an inner shaft distal tip 18, and a first distal balloon 20 is located proximal to the inner shaft distal tip 18 along the catheter longitudinal axis. At the most proximal end of the inner shaft is a plunger 22. The outer shaft 14 has at its most distal end an outer shaft distal tip 23, and a second proximal balloon 24 is located proximal to the outer shaft distal tip 23 along the catheter longitudinal axis 16. The outer shaft has a handle 26 which is fixed to the outer shaft and a hub 28 which is fixed to the outer shaft, but longitudinally movable along the inner shaft. At the proximal end of the catheter are ports 30. The ports 30 communicate with the lumens of the inner shaft 12 and outer shafts 14 allowing for access into the catheter by elements including, but not limited to guidewires, balloon inflation sources, and/or agent delivery sources. Lumens generally extend from the proximal ends to open distal ends of the inner or outer shaft, 12 or 14 respectively, or from a port 30 which communicates with the lumen to allow access to elements including guidewires, balloon inflation sources and/or agent delivery or collection sources.

As illustrated in FIG. 3A, the outer shaft 14 has an outer shaft interior wall 40 and an outer shaft exterior wall 42. The outer shaft interior wall 40 defines an outer shaft central lumen 44. Outer shaft peripheral lumens 46 are formed within outer shaft 14 and are located between the outer shaft interior wall 40 and outer shaft exterior wall 42. As illustrated in FIG. 3B, the inner shaft 12 has an inner shaft interior wall 32 and an inner shaft exterior wall 34. The inner shaft interior wall 32 defines an inner shaft central lumen 36. Inner shaft peripheral lumens 38 are formed within the inner shaft 12 and are located between the inner shaft interior wall 32 and inner shaft exterior wall 34. Alternatively, lumens may be formed in the inner shaft 12 so that the lumens are arranged axially around the catheter longitudinal axis 16.

As illustrated in FIG. 3C, when assembled, the inner shaft 12 is located within the outer shaft central lumen 44 of the catheter. The catheter of the present invention may be used with an outer guide catheter 50 to guide the catheter to the pericardial membrane.

As illustrated in FIG. 3D, the inner shaft distal tip 18 can have orifices 48 that extend from the inner shaft central lumen 36 and/or the inner shaft peripheral lumens (not shown) to the inner shaft exterior wall 34 for the delivery or collection of agents to the pericardial space.

The present invention also contemplates a method of using a catheter for the delivery or the collection of agents from a target biological space in vivo. When used to catheterize the pericardial space the balloons act to seal off the passageway in the pericardium made by the inner shaft distal tip. This is to prevent pericardial fluid from flowing into the atrium, to prevent blood in the atrium from flowing into the pericardial space, and to insure that the therapeutic agent delivered stays within the space and is not systemically administered. Further, the balloons act to stabilize the catheter within the pericardial space by being inflated against the inner and outer pericardial membrane.

The catheter of the present invention can be used to approach the pericardial space via the right auricle, as described by Verrier. This method involves reaching the pericardial space by guiding a catheter through one of the vena cavae to the right atrium, then into the right auricle. By this approach, the catheter is substantially parallel to the wall of the pericardium, so that when the catheter is advanced through the pericardium there is a low risk of piercing the underlying heart. Alternatively, the catheter of the present invention can be used to access the pericardial space via the ventricular space. For example, the catheter can be used to access the right atrium, pierce the septum and thereafter access the left ventricle. Once in the left ventricle, the catheter is used to pierce the ventricular wall to access the pericardial space.

As illustrated in FIGS. 4A–D, the catheter 10 when inserted/introduced to the tissue preferably has the inner shaft 12, distal balloon 20, and inner shaft distal tip 18 retracted into the outer shaft 14 (FIG. 4A). The user advances the catheter toward the pericardial membrane using the handle 26 to apply forward pressure (thick arrow). When the catheter is advanced so that it is proximal to the pericardial membrane the inner shaft 12 is moved longitudinally relative to the outer shaft 14 by applying forward pressure to the plunger 22. The inner shaft distal tip 18 is then moved forward to pierce the pericardial membrane. The user advances the inner shaft until distal balloon 20 is situated within the pericardial space (thin arrow; FIG. 4B). The distal balloon 20 is then inflated by a balloon inflation source in communication with a port 30 and lumen in the inner shaft 12 (FIG. 4C). The user advances the outer shaft 14 by moving the hub 28 longitudinally forward (open arrow) relative to the inner shaft 12 until the proximal balloon 24 is firmly opposed to the outer surface of the pericardial membrane. The proximal balloon 24 is then inflated by a balloon inflation source in communication with a port 30 and lumen in the outer shaft 14 (FIG. 4D). Agents can then be infused or collected via the inner shaft distal tip 18 in the pericardial space.

Alternatively, as discussed previously, the catheter can also be used to access the pericardial space by entering the right atrium, crossing the septum and entering the left ventricle. As discussed above, the catheter inner shaft distal tip 18 is moved forward to pierce the pericardial membrane and the inner shaft is advanced until distal balloon 20 is situated within the pericardial space. The distal balloon 20 is inflated, the outer shaft 14 is advanced until the proximal balloon 24 is firmly opposed to the outer surface of the pericardial membrane. The proximal balloon 24 is then inflated and agents can then be infused or collected via the inner shaft distal tip in the pericardial space.

Detailed Description of the Second Embodiment

In an alternate embodiment illustrated in FIGS. 5A–D, catheter 110 has an inner shaft 112 longitudinally movable relative to outer shaft 114. However, in this embodiment outer shaft 114 further includes a proximal pusher portion 115 which is separable from the distal end portion 116 of the outer shaft 114 to reveal inner shaft 112. Outer shaft 114 has distal tip 118, which can be a needle designed to pierce membranes and tissue, and a first balloon 120 proximal to the distal tip 118 and inner shaft 112 has distal tip 123 and second balloon 124 proximal to distal tip 123. As with catheter 10, outer shaft 114 of catheter 110 has a handle 26 which is fixed to proximal pusher portion 115 of outer shaft 114 and provides longitudinal movement to pusher 115. In most other respects, catheter 110 has the same features at its proximal end (not shown) as catheter 10.

Figure 5A:
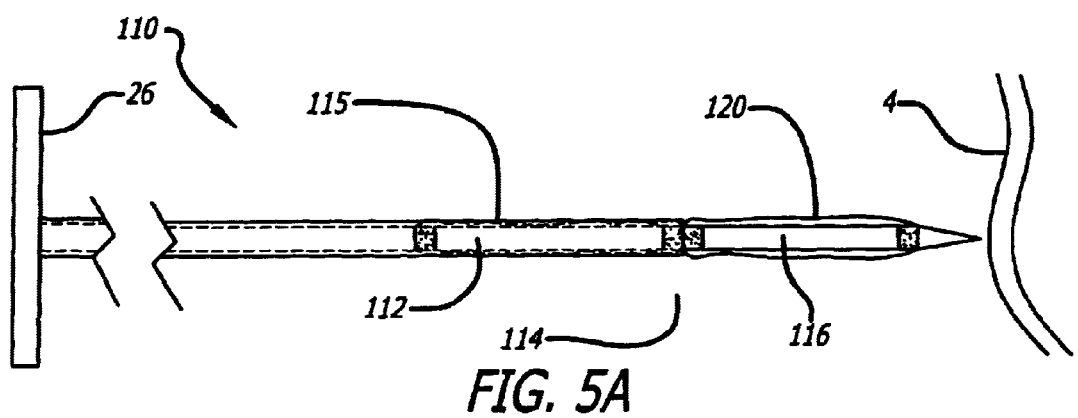
FIGS. 5A–5D are side views of the distal end of an another exemplary embodiment of the present invention in various stages of application.
Figure 5B:
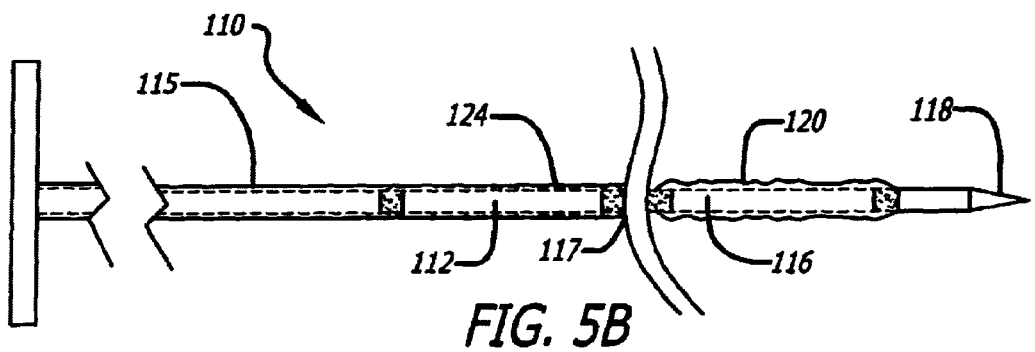

Proximal pusher portion 115 has a distal end 117 that is engageable and retractable with the distal end portion 116 of outer shaft 114 by a threading or locking mechanism and in other ways known to those of skill in the art. As illustrated in FIG. 5A, when catheter 110 is introduced into the body proximal pusher portion 115 is engaged with distal end portion 116 of outer shaft 114 and inner shaft 112 is contained within outer shaft 114. The user applies forward pressure to handle 26 to advance catheter 110 towards the pericardial membrane 4. Outer shaft distal tip 118 is moved forward to pierce the pericardial membrane and outer shaft 114 is advanced forward until first balloon 120 is within the pericardial space (FIG. 5B).

Figure 5C:
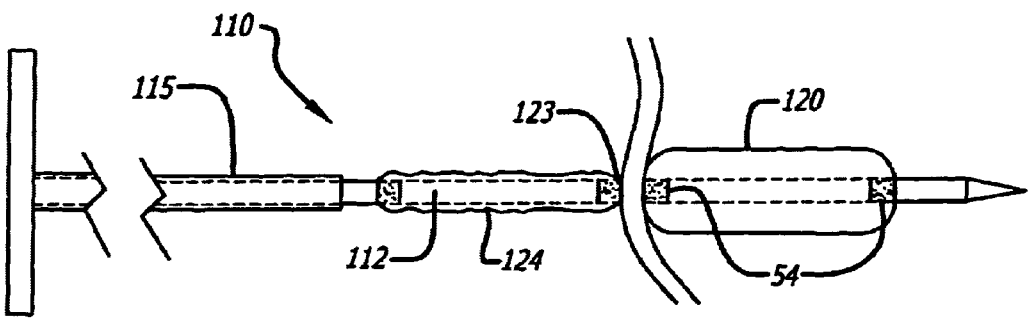
Figure 5D:
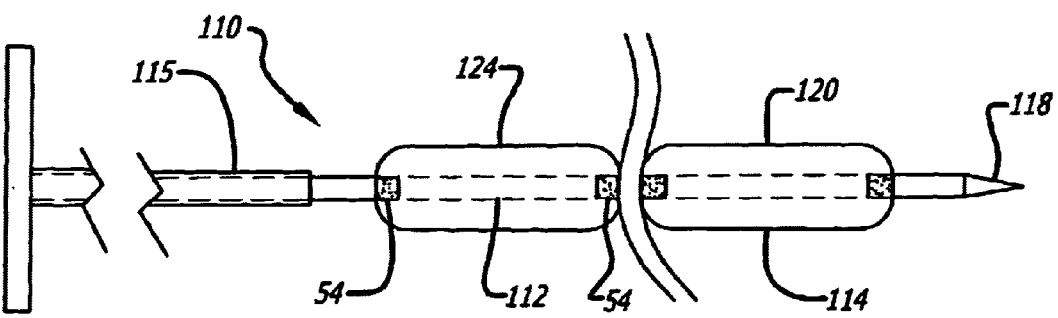

As illustrated in FIG. 5C, first balloon 120 is inflated by a balloon inflation source in communication with a proximal port and lumen (not shown) as in catheter 10. Proximal pusher portion 115 is then retracted, revealing inner shaft 112 and second balloon 124. Second balloon 124 is inflated in similar fashion to catheter 10 and agents can be infused into or collected from the pericardial space. Upon completion of the procedure, the second balloon 124 is deflated and pusher 115 is advanced distally to enclose inner shaft 112 and engage with distal end portion 116 of outer shaft 114. First balloon 120 is deflated and catheter 110 can then be removed from the body.

Detailed Description of the Third Embodiment

As illustrated in FIG. 6, a third embodiment of the catheter 610, generally comprises an inner shaft 612 longitudinally movable within an outer shaft 614 along the catheter longitudinal axis 616. The inner shaft 612 defined by an inner shaft interior wall 661 defining inner shaft lumen 613, and an inner shaft exterior wall 662 having at its most distal end an inner shaft distal tip 618. Inflation ports 665 and 667 provide access to inner shaft lumen 613. A pliable inflatable balloon 650, positioned to enclose inflation ports 665 and 667, is attached to inner shaft exterior wall at the most proximal end of the inner shaft along the longitudinal axis of the catheter 610. The outer shaft 614, defined by outer shaft interior wall 657 defining outer shaft lumen 615, and outer shaft exterior wall 658, has at its most distal end an outer shaft distal tip 621. The outer shaft 614 has a handle 626 which is fixed to the outer shaft and a hub 628 which is fixed to the outer shaft, but longitudinally movable along the inner shaft. At the proximal end of the catheter are ports 630. The ports 630 communicate with inner shaft lumen 613 and outer shaft lumen 615 allowing for access into the catheter by elements including, but not limited to guidewires, balloon inflation sources and/or agent delivery sources. Lumens 613 and 615 generally extend from the proximal ends to open distal ends of the inner or outer shaft, 612 or 614 respectively, or from a port 630 which communicates with lumens 613 and 615, respectively, to allow access to elements including guidewires, wire support deployment mechanisms, balloon inflation sources, and/or agent delivery or collection sources.

As illustrated and in accordance with the Verrier catheter insertion technique, when catheter 610 is introduced into the body, inner shaft 612 is contained within outer shaft 614. The user applies forward pressure to handle 626 to advance catheter 610 towards the pericardial membrane 604. Outer shaft 614 is positioned proximal to pericardial membrane as inner shaft distal tip 618 is moved forward to pierce the pericardial membrane. Outer shaft 614 is then advanced forward until inner shaft distal tip 618 is within the pericardial space. Pliable inflatable balloon 650 is inflated by a balloon source in communication with port 630 and lumen in inner shaft 612. Pliable inflatable balloon 650 serves to seal the opening created in the pericardial membrane 604, thereby permitting isolated infusion of medicament.

Upon completion of the procedure, pliable inflatable balloon 650 is deflated. Inner shaft 612 retracts within outer shaft 614. Catheter 610 can then be removed from the body.

As discussed with respect to previous embodiments, the catheter can also be used to access the pericardial space by entering the right atrium, crossing the septum and entering the left ventricle.

Detailed Description of the Fourth Embodiment

Figure 7A:
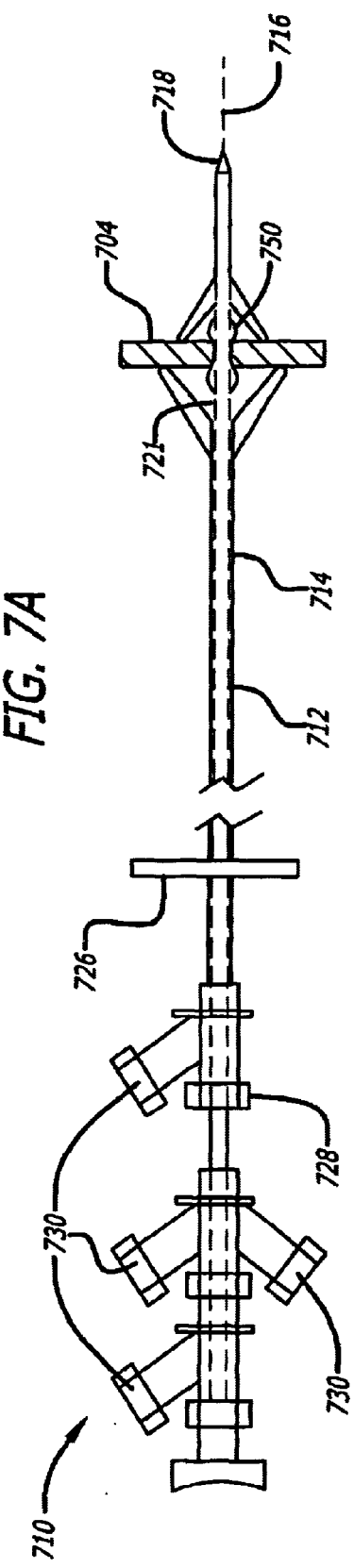
FIGS. 7A–7C are side views of A) another exemplary embodiment of the present invention; B) the distal portion of the outer shaft of the present invention; C) the inner shaft extended beyond the outer shaft.
Figure 7C:
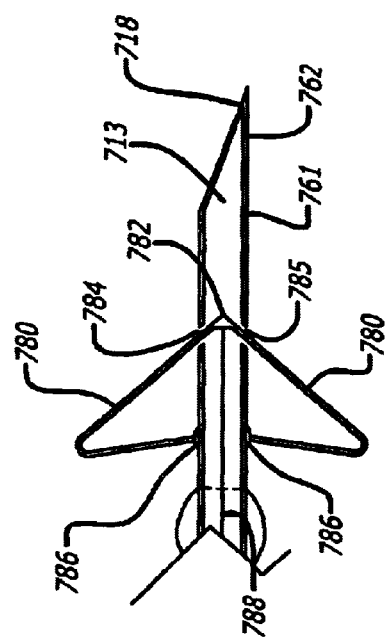
Figure 7B:
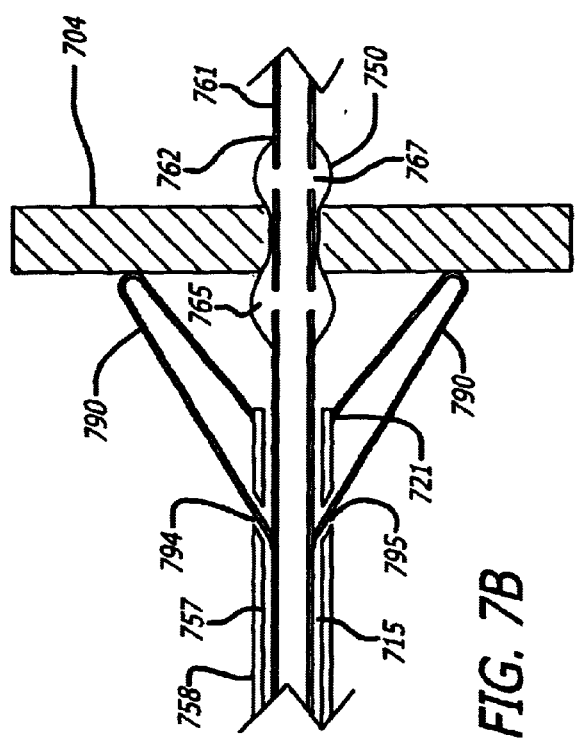

As illustrated in FIG. 7, a fourth embodiment of the catheter 710, generally comprises an inner shaft 712 longitudinally movable within an outer shaft 714 along the catheter longitudinal axis 716. The inner shaft 712 defined by an inner shaft interior wall 761 defining an inner shaft lumen 713, and an inner shaft exterior wall 762 having at its most distal end an inner shaft distal tip 718. Inflation ports 765 and 767 provide access to inner shaft lumen 713. A pliable inflatable balloon 750, positioned in fluid communication with inflation ports 765 and 767 is attached to inner shaft exterior wall 762 at the most proximal end of the inner shaft 712 along the longitudinal axis 716 of the catheter 710. A first wire support 780 has a distal portion positioned proximal to inner shaft distal tip 718, and in communication with first wire support deployment mechanism 782 through ports 784 and 785, whereby the proximal portion flexibly attached to inner shaft exterior wall 786. First wire support deployment mechanism is in communication with outer shaft handle 726 through a deployment conduit 788. Deployment conduit 788 is used to slidably urge deployment mechanism 782 towards deployment ports 784 and 785, resulting in deployment of first wire support 780. The outer shaft 714 enclosing the inner shaft 712 is defined by an outer shaft interior wall 757 defining outer shaft lumen 715, and outer shaft exterior wall 758. The outer shaft 714 has at its most distal end an outer shaft distal tip 721. Second wire support 790 distal portion is positioned along the catheter longitudinal axis 716 adjacent to and flexibly attached to outer shaft exterior wall 758. Second wire support proximal portion communicates with inner shaft exterior wall 757 through ports 794 and 795. The outer shaft has a handle 726 which is fixed to the outer shaft and a hub 728 which is fixed to the outer shaft, but longitudinally movable along the inner shaft. At the proximal end of the catheter are ports 730. The ports 730 communicate with the lumen 713 of the inner shaft 712 and outer shaft lumen 715 allowing for access into the catheter by elements including, but not limited to guidewires, wire support deployment mechanisms, balloon inflation sources and/or agent delivery sources. Lumens 713 and 715, respectively, generally extend from the proximal ends to open distal ends of the inner or outer shaft, 712 or 714 respectively, or from a port 730 which communicates with the lumens 713 and 715, respectively, to allow access to elements including guidewires, wire support deployment mechanisms, balloon inflation sources, and/or agent delivery or collection sources.

First wire support deployment mechanism 782 is engageable and retractable by a threading or locking mechanism and in other ways known to those of skill in the art. When catheter 710 is introduced into the body first wire support 782 is retracted and positioned along the longitudinal axis of the catheter 710 proximal to inner shaft 712, which is contained within outer shaft 714. Second wire support 790 is retracted and positioned proximal to outer shaft exterior wall 758 along the longitudinal axis of the catheter 710. The user applies forward pressure to handle 726 to advance catheter 710 towards the pericardial membrane 704. Inner shaft distal tip 718 is moved forward to pierce the pericardial membrane 704. Once outer shaft distal tip 721 is positioned proximal to pericardial membrane 704, inner shaft distal tip 418 is advanced through the pericardial membrane 704. Forward advancement of inner shaft 712 slidably urges second wire support 790 through deployment port 794 and 795, thereby deploying second wire deployment anchor 491. Outer shaft 714 is advanced forward until inner shaft distal tip 718 is within the pericardial space and second wire support 790 contacts pericardial membrane 704. First wire support 780 is deployed to stabilize catheter 710. Pliable inflatable balloon 750 is inflated thereby isolating the pericardial space from the right atrium. Pliable inflatable balloon 750 is inflated by a balloon source in communication with ports 784 and 785 and lumen in inner shaft 712, and medicament is infused into the isolated pericardial region. Upon completion of the procedure, pliable inflatable balloon 750 is deflated. Inner shaft distal tip 718 and first and second wire supports, 780 and 790 respectively, are retracted. Catheter 710 can then be removed from the body.

Detailed Description of the Fifth Embodiment

As illustrated in FIG. 8, a fifth embodiment of the catheter 810, generally comprises an inner shaft 812 longitudinally movable within an outer shaft 814 along the catheter longitudinal axis 816. The inner shaft 812 is defined by an inner shaft interior wall 861 defining an inner shaft lumen 813, and an inner shaft exterior wall 862 having at its most distal end an inner shaft distal tip 818. A first wire support 880 positioned proximal to the most distal end of the inner shaft 812 along the longitudinal axis 816 of the catheter 810, has a distal portion in communication with first wire support deployment mechanism 882 through a deployment ports 865 and 867, and a proximal portion flexibly attached to inner shaft exterior wall 886. First wire support deployment mechanism is in communication with outer shaft handle 826 through a deployment conduit 888. Deployment conduit 888 is used to slidably urge deployment mechanism 882 towards deployment ports 865 and 867 resulting in first wire support 880 deployment. The outer shaft 814 enclosing the inner shaft 812 is defined by an outer shaft interior wall 857 and outer shaft exterior wall 858. The outer shaft 814 has at its most distal end an outer shaft distal tip 821. Second wire support 890 distal portion is positioned along the catheter longitudinal axis 816 adjacent to and flexibly attached to outer shaft exterior wall 858. Second wire support proximal portion communicates with inner shaft exterior wall 857 through ports 894 and 895. The outer shaft has a handle 826 which is fixed to the outer shaft and a hub 828 which is fixed to the outer shaft, but longitudinally movable along the inner shaft. At the proximal end of the catheter are ports 830. The ports 830 communicate with the lumen 813 of the inner shaft 812 and outer shaft lumen 815 allowing for access into the catheter by elements including, but not limited to guidewires, wire support deployment mechanisms, and/or agent delivery sources. Lumens 813 and 815, respectively, generally extend from the proximal ends to open distal ends of the inner or outer shaft, 812 or 814 respectively, or from a port 830 which communicates with the lumens 813 and 815, respectively, to allow access to elements including guidewires, wire support deployment mechanisms, and/or agent delivery or collection sources.

Figure 9A:
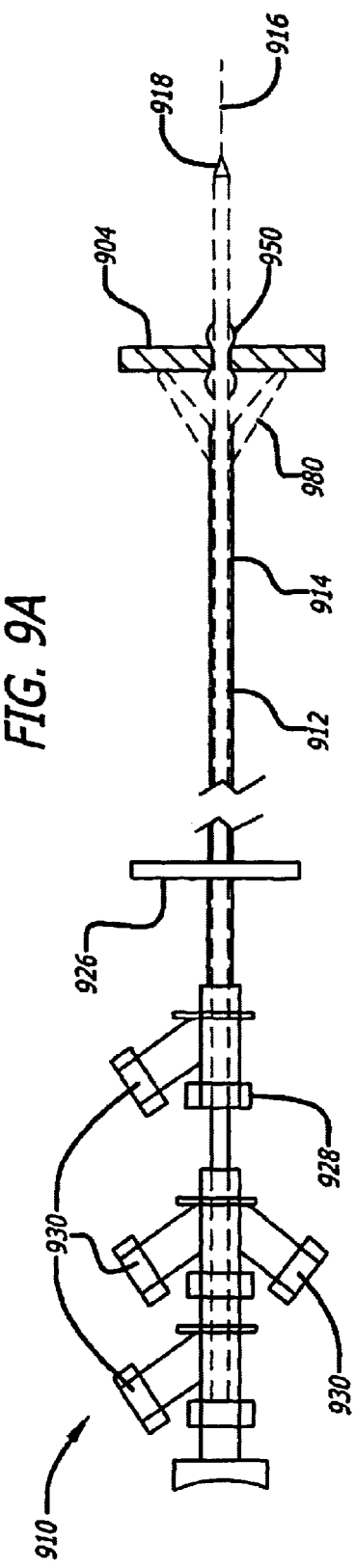
FIGS. 9A–9C are side views of A) another exemplary embodiment of the present invention; B) the distal portion of the outer shaft containing the non-deployed inner shaft; C) the distal portion of the outer shaft with the inner shaft deployed.
Figure 9C:
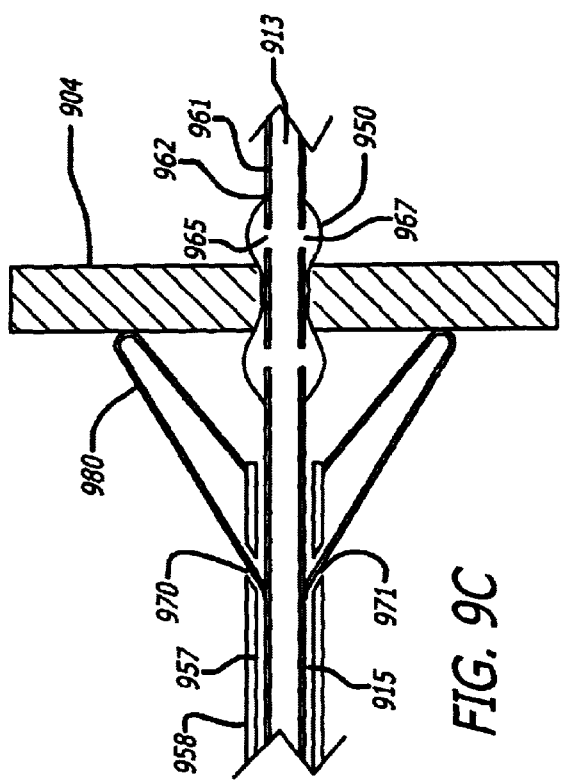
Figure 9B:
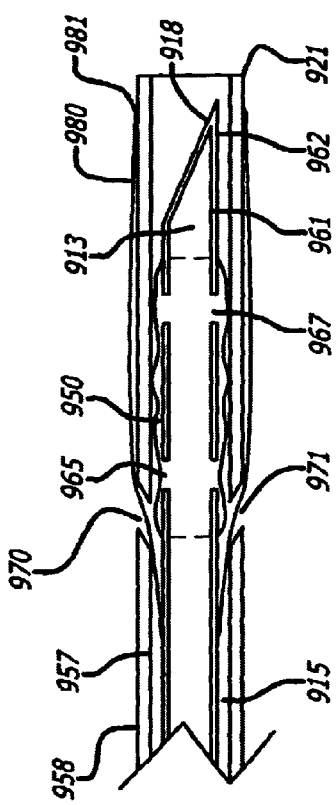

First wire support deployment mechanism 882 is engageable and retractable by a threading or locking mechanism and in other ways known to those of skill in the art. When catheter 810 is introduced into the body first wire support 882 is retracted positioned along the longitudinal axis of the catheter 810 proximal to inner shaft 812, which is contained within outer shaft 814. Second wire support 890 is retracted; positioned proximal to outer shaft exterior wall 858 along the longitudinal axis of the catheter 810. The user applies forward pressure to handle 826 to advance catheter 810 towards the pericardial membrane 804. Inner shaft distal tip 818 is moved forward to pierce the pericardial membrane 804. Once outer shaft distal tip 821 is positioned proximal to pericardial membrane 804, inner shaft distal tip 818 is advanced through the pericardial membrane 804. Forward advancement of inner shaft distal tip 818 slidably urges second wire support 890 through deployment ports 894 and 895, structurally interacting with second wire deployment anchor 891. Outer shaft 814 is advanced forward until inner shaft distal tip 818 is within the pericardial space and second wire support 890 contacts pericardial membrane 804. First wire support 880 is deployed to stabilize catheter 810, and medicament is injected into the pericardial area. Upon completion of the procedure, inner shaft distal tip 818 and first and second wire supports, 880 and 890 respectively, are retracted. Catheter 810 can then be removed from the body.
Detailed Description of the Sixth Embodiment As illustrated in FIG. 9, a sixth embodiment of the catheter 910, generally comprises an inner shaft 912 longitudinally movable within an outer shaft 914 along the catheter longitudinal axis 916. The inner shaft 912 defined by an inner shaft interior wall 961 defining inner shaft lumen 913, and an inner shaft exterior wall 962 having at its most distal end an inner shaft distal tip 918. Inflation ports 965 and 967 provide access to inner shaft lumen 913. A pliable inflatable balloon 950, positioned to enclose inflation ports 965 and 967, is attached along the longitudinal axis of the catheter 910. The outer shaft 914 enclosing the inner shaft is defined by an outer shaft interior wall 957 and outer shaft exterior wall 958 defining outer shaft lumen 915. Outer shaft 914 has at its most distal end an outer shaft distal tip 921, and a wire support 980 attached to outer shaft exterior wall 958, and is functionally connected to inner shaft exterior wall 962 through deployment ports 970 and 971 respectively. Wire support 980 is located proximal to the outer shaft distal tip 921 along the catheter longitudinal axis 916. The outer shaft 914 has a handle 926 which is fixed to the outer shaft and a hub 928 which is fixed to the outer shaft 914, but longitudinally movable along the inner shaft. At the proximal end of the catheter are ports 930. The ports 930 communicate with lumens 912 and 914 respectively, thereby allowing for access into the catheter by elements including, but not limited to guidewires, wire support deployment mechanisms, balloon inflation sources and/or agent delivery sources. Lumens generally extend from the proximal ends to open distal ends of the inner or outer shaft, 912 or 914 respectively, or from a port 930, to allow access to elements including guidewires, wire support deployment mechanisms, balloon inflation sources, and/or agent delivery or collection sources.

Wire support deployment mechanism 980 has a distal end 981 that is flexibly attached to outer shaft exterior wall 958 proximal to outer shaft distal end portion 921 of outer shaft 914 by a threading or locking mechanism and in other ways known to those of skill in the art. When catheter 910 is introduced into the body wire support deployment mechanism 980 is retracted, position proximal to outer shaft exterior wall 958 along the longitudinal axis of catheter 910, and having inner shaft 912 is contained within outer shaft 914. The user applies forward pressure to handle 926 to advance catheter 910 towards the pericardial membrane 904. As inner shaft distal tip 918 is moved forward, wire support 980 slidably deploys through deployment ports 970 and 971 respectively, and engages the pericardial tissue thereby providing support to catheter 910 forward advancement continuing until inner shaft distal tip 918 is within the pericardial space. Pliable inflatable balloon 950 is inflated by a balloon inflation source in communication with port 930 and medicament is then infused into the isolated pericardial region. Upon completion of the procedure, pliable inflatable balloon 950 is deflated and inner shaft distal end 918 and wire support 980 are retracted. Catheter 910 can then be removed from the body.

In all of the aforementioned embodiments the catheter can be used to access the pericardial space using the Verrier technique or, alternatively, by entering the right atrium, crossing the septum and entering the left ventricle.

Although the present invention has been described in terms of the illustrated embodiment above, numerous modifications and/or additions to the above-described illustrated embodiments would be readily apparent to one skilled in the art.

The catheter inner shaft and outer shaft can be made of various materials known to those skilled in the art, including, but not limited to nylon, Pebax and polyethelene. The shaft materials can be selected so as to maximize column strength through the longitudinal length of the shaft. Further, the shaft materials can be braided, so as to provide sufficient column strength. The shaft materials can also be selected so as to allow the inner shaft to move smoothly within the outer shaft of the catheter and/or to allow the device to move smoothly within a guide catheter. The shaft materials can also be selected so as to maximize bonding of the shafts to the balloon materials.

In some embodiments, the catheter 10/110 can be used with a guide catheter 50 to assist in guiding the catheter to the intended target. Such guide catheters are preferably about 6–8 Fr in diameter.

The catheter outer shaft exterior wall 42 is preferably between about 3–7 Fr. in diameter. The outer shaft exterior wall 42 is most preferably about 4.5 Fr. The outer shaft interior wall 40 is preferably between about 2–5 Fr. in diameter. The outer shaft interior wall 40 is most preferably about 3 Fr.

The catheter inner shaft exterior wall 34 is preferably between about 2–5 Fr. in diameter. The inner shaft exterior wall 34 is most preferably about 3 Fr. The inner shaft interior wall 32 is preferably between about 1–4 Fr. in diameter. The inner shaft interior wall is most preferably about 2 Fr.

The inner shaft distal tip 18/118. can be either blunt or sharp. Further, inner shaft distal tip 18/118 can be open or closed at the most distal end. Where the inner shaft distal tip is sharp, the tip can be a needle designed to pierce membranes and tissue. The needle can be made of various appropriate materials including, but not limited to, stainless steel or titanium. The needle can be hollow and can have orifices 48 to provide access via a lumen to the pericardial space for the delivery or collection of agents from the pericardial space. The distal tip can be radio-opaque to aid in the visualization during a catheterization.

The distal and proximal balloons, 20/120 & 24/124, can be made of various materials known to those of skill in the art, including, but not limited to, latex, Kraton, polyurethane or any other biocompatible, elastomeric material, or other soft materials. The materials of the balloons may be selected so as to maximize pliability and/or reduce the risk of damage to tissues. Various balloon inflation sources known to those of skill in art can be used, such as a hand syringe in communication with lumens of the inner and/or outer shafts 12 & 14 via the appropriate proximal ports.

The distal balloon 20 and the proximal balloon 24, when inflated, are preferably between about 3–5 mm in diameter. The balloons are most preferably about 3 mm in diameter. The balloons are preferably between about 1–2 cm in length. The balloons are most preferably about 1 cm long. However, the length of the balloons can be selected to be as short as possible so as to minimize tissue damage.

The catheter 10/110 may have a plurality of ports 30 which communicate with the lumens 36, 38, 44, and 46 within the inner shaft 12/112 and outer shaft 14/114. In one embodiment, the inner shaft central lumen 36 provides a channel for a guidewire 52, a first inner shaft peripheral lumen 38 provides a channel for gasses or liquids to fill the distal balloon 20, and a second inner shaft peripheral lumen 38 provides a channel for the agent to be delivered to the pericardial space via the inner shaft distal tip 18 and out of the orifices 48. The outer shaft central lumen 44 contains the inner shaft 12 within it, and a first outer shaft peripheral lumen 46 provides a channel for contrast media or saline to fill the proximal balloon 24.

In an alternate embodiment, the inner shaft central lumen 36 provides a channel for a guidewire 52. Once the catheter 10/110 is in place, the guidewire 52 can be retracted from the inner shaft central lumen 36, and the agent can be delivered to the biological space via the inner shaft central lumen 36 to the inner shaft distal tip 18/118.

In another alternate embodiment, one or both balloons could be made of microporous materials so that agents are delivered by the balloons instead of or in addition to the inner shaft distal tip 18/118 and or orifices 48.

In another alternate embodiment, the guidewire 52 may be hollow and serve as a pathway for the delivery of agents during catheter use or may remain in place in the pericardial space after removal of the catheter.

The catheter can be visualized by thoroscopic, fluroscopic or ultrasonic visualization to determine its position in vivo, as described by Verrier in Persistent primary coronary dilation induced by transatrial delivery of nitroglycerin into the pericardial space: A novel approach for local cardiac drug delivery. *J of Am. Coll. Cardiol.* (1999), herein incorporated by reference. Alternatively, imaging systems such as the Webster-Biosense NOGA system or an ultrasound system such as the Mayo-Accuson Inside-Out system may be used to determine the position of the catheter in vivo. Further, confirmation of access to the pericardial space can be confirmed by injection of contrast dye.

In some embodiments inner shaft 12/112 and/or outer shaft 14/114 may include marker bands 54 which can be used to detect the position of the balloons and/or shafts relative to one another or relative to the pericardial space. The marker bands can be made of materials including, but not limited to platinum, gold or tantalum, which may incorporated into the shaft walls or placed on the surface. In some embodiments, a guidewire 52 can be advanced through the catheter into the pericardial space to confirm the position in the pericardial space. In some embodiments, radio-opaque markers at the inner shaft distal end 18/118 can be used to visualize the location of the catheter using fluoroscopy during the procedure.

Where guidewires 52 are used with the catheter, the guidewires can be made of materials including, but not limited to stainless steel. The guidewire materials can be selected such that the surface of the guidewire moves smoothly within the lumen. The guidewires are preferably from about 0.014–0.038 inches and most preferably from about 0.014 to about 0.018 inches in diameter.

Agents include any one of or a combination of several agents which are gas, liquid or solid and which may be delivered or collected from the pericardial space for therapeutic or diagnostic purposes. Therapeutic agents include biologically active substances, or substances capable of eliciting a biological response, including, but not limited to endogenous substances (growth factors or cytokines, including, but not limited to basic fibroblast growth factor, acidic fibroblast growth factor, vascular endothelial growth factor, angiogenic factors), viral vectors, DNA capable of expressing proteins, sustained release polymers, unmodified or modified cells. Therapeutic agents include angiogenic agents which induce the formation of new blood vessels. For diagnostic purposes, imaging fluid may be injected into the right atrium and the pericardial space for fluid imaging of the heart and pericardial fluid may be withdrawn for diagnostic analysis. Further, electrical devices may be implanted to detect electrical signals in the heart or deliver them to the heart.

The rate of delivery of agents can be selected so as to reduce tissue damage. The rate of delivery of agent can depend upon at least the size and number of orifices and the pressure under which the agent is passed through the orifices. The rate of delivery can be controlled by osmotic pump. An agent delivery or collection device can be a syringe or infusion pump for slow, precise, measured delivery, in communication with a lumen via a port 30 in the inner shaft 12/112.

Other biological spaces which may be accessed by this catheter include but are not limited to the sub-dural and sub-arachnoid spaces of the central nervous system and the bladder. In closing, it is noted that specific illustrative embodiments of the invention have been disclosed hereinabove. However, it is to be understood that the invention is not limited to these specific embodiments. Accordingly, the invention is not limited to the precise embodiments described in detail hereinabove. With respect to the claims, it is applicant's intention that the claims not be interpreted in accordance with the sixth paragraph of 35 U.S.C. §112 unless the term "means" is used followed by a functional statement. Further, with respect to the claims, it should be understood that any of the claims described below can be combined for the purposes of the invention.

What is claimed is:

1. A catheter for delivering agents to a defined biological space in vivo comprising:
    an inner catheter shaft defining at least one inner shaft lumen and having an inner shaft distal tip configured to pierce a biological membrane proximate to the biological space;
    an outer catheter shaft defining at least one outer shaft lumen and having an outer shaft distal tip;
    said inner catheter shaft longitudinally movable within and with respect to said outer catheter shaft; and
    at least one deployable support member non-detachably secured to at least one of said inner catheter shaft and said outer catheter shaft.

2. A catheter of claim 1, wherein said at least one deployable support member comprises at least one inflatable balloon in communication with at least one of said lumens of said inner catheter shaft or said outer catheter shaft.

3. A catheter of claim 2, wherein said at least one deployable support member comprises said at least one inflatable balloon disposed on said inner catheter shaft and in communication with said at least one inner shaft lumen.

4. A catheter of claim 2, wherein said at least one deployable support member comprises said at least one inflatable balloon disposed on said outer catheter shaft and in communication with said at least one outer shaft lumen.

5. A catheter of claim 2, wherein said at least one deployable support member comprises said at least one inflatable balloon disposed on said inner catheter shaft and in communication with said at least one inner shaft lumen, and said at least one deployable support member comprises said at least one inflatable balloon disposed on said outer catheter shaft and in communication with said at least one outer shaft lumen.

6. A catheter of claim 1, wherein said at least one deployable support member comprises at least one deployable wire support in communication with at least one of said lumens of said inner shaft or said outer shaft.

7. A catheter of claim 6, wherein said at least one deployable support member comprises said at least one deployable wire support disposed on said inner shaft and in communication with said at least one inner shaft lumen.

8. A catheter of claim 6, wherein said at least one deployable support member comprises said at least one deployable wire support disposed on said outer shaft and in communication with said at least one outer shaft lumen.

9. A catheter of claim 6, wherein said at least one deployable support member comprises said at least one deployable wire support disposed on said inner shaft and in communication with said at least one inner shaft lumen, and said at least one deployable support member comprises said at least one deployable wire support disposed on said outer shaft and in communication with said at least one outer shaft lumen.

10. A catheter of claim 1, wherein said inner shaft distal tip is a needle.

11. The catheter of claim 1, wherein said catheter comprises at least one port positioned proximate to the proximal portion of said catheter and in communication with one of said lumens in said inner catheter shaft, and wherein said lumen is for delivery of an agent to a biological space.

12. A catheter of claim 11, wherein the agent is a therapeutic agent.

13. A catheter of claim 11, wherein the agent is an angiogenic agent.

14. A catheter of claim 11, wherein said at least one port is in communication with at least one of said lumens of said inner catheter shaft and said outer catheter shaft and wherein at least one of said lumens is for the inflation of said inflatable balloon.

15. A catheter of claim 11 wherein said at least one port is in communication with at least one of said lumens of said inner shaft or said outer shaft and wherein at least one of said lumens is for the deployment of said deployable wire support.

16. A catheter of claim 1, wherein said inner shaft distal tip has orifices formed therein for the delivery of an agent from said lumen of said inner catheter shaft to the biological space.

17. A catheter of claim 1 further comprising at least one inflatable sealing balloon in communication with at least one of said lumens of said inner catheter shaft or said outer catheter shaft.

18. A catheter of claim 17, further comprising at least one inflatable balloon positioned on said inner catheter shaft and in communication with said at least one inner shaft lumen.

19. A catheter of claim 17, wherein said catheter disposes said at least one deployable support member comprising at least one inflatable balloon in communication with at least one said outer shaft and having said at least one inflatable sealing balloon disposed on said inner shaft and in communication with said at least one inner shaft lumen.

20. A catheter of claim 17, wherein said catheter disposes said at least one deployable support member comprising at least one inflatable balloon in communication with at least one said inner shaft and having said at least one inflatable sealing balloon disposed on said outer shaft and in communication with said at least one outer shaft lumen.

21. A catheter of claim 17, further comprising at least one inflatable balloon positioned on said outer catheter shaft and in communication with said at least one outer shaft lumen.

22. A catheter of claim 17, further comprising at least one inflatable balloon positioned on said inner catheter shaft and in communication with said at least one inner shaft lumen, and at least one inflatable balloon positioned on said outer catheter shaft and in communication with said at least one outer shaft lumen.

23. A catheter of claim 17, wherein said catheter disposes said at least one deployable support member comprising at least one inflatable balloon in communication with at least one said inner shaft and having said at least one inflatable sealing balloon disposed on said outer shaft and in communication with said at least one outer shaft lumen, and disposing said at least one deployable support member comprising at least one inflatable balloon in communication with at least one said outer shaft and having said at least one inflatable sealing balloon disposed on said outer shaft and in communication with said at least one outer shaft lumen.

24. A catheter of claim 17, further comprising at least one deployable wire support in communication with at least one of said inner catheter shaft and said outer catheter shaft and having said at least one inflatable sealing balloon disposed on at least one of said inner catheter shaft and said outer catheter shaft.

25. A catheter of claim 17, wherein said catheter disposes said at least one deployable support member comprising at least one deployable wire support in communication with at least one said outer shaft and having said at least one inflatable sealing balloon disposed on said inner shaft and in communication with said at least one inner shaft lumen.

26. A catheter of claim 17, wherein said catheter disposes said at least one deployable support member comprising at least one deployable wire support in communication with at least one said inner shaft and having said at least one inflatable sealing balloon disposed on said outer shaft and in communication with said at least one outer shaft lumen.

27. A catheter of claim 17, wherein said catheter disposes said at least one deployable support member comprising at least one deployable wire support in communication with at least one said outer shaft and having said at least one inflatable sealing balloon disposed on said outer shaft and in communication with said at least one outer shaft lumen.

28. A catheter of claim 17, wherein said catheter disposes said at least one deployable support member comprising at least one deployable wire support in communication with at least one said inner shaft and having said at least one inflatable sealing balloon disposed on said inner shaft and in communication with said at least one inner shaft lumen, and disposing said at least one deployable support member comprising at least one deployable wire support in communication with at least one said outer shaft and having said at least one inflatable sealing balloon disposed on said outer shaft and in communication with said at least one outer shaft lumen.

29. A catheter of claim 17, wherein said catheter disposes said at least one deployable support member comprising at least one deployable wire support in communication with at least one said inner shaft and having said at least one inflatable sealing balloon disposed on said outer shaft and in communication with said at least one outer shaft lumen, and disposing said at least one deployable support member comprising at least one deployable wire support in communication with at least one said outer shaft and having said at least one inflatable sealing balloon disposed on said outer shaft and in communication with said at least one outer shaft lumen.

30. A catheter for delivering agents to a defined biological space in vivo comprising:
an inner catheter shaft defining at least one inner shaft lumen and having an inner shaft distal tip;
an outer catheter shaft defining at least one outer shaft lumen and having an outer shaft distal tip;
said inner catheter shaft longitudinally movable within and with respect to said outer catheter shaft;
said outer catheter shaft comprising a proximal pusher portion and a distal end portion, said proximal pusher portion configured to be retractable from said distal end portion to uncover said inner catheter shaft; and
at least one deployable support member non-detachably attached to at least one of said inner catheter shaft and said outer catheter shaft.

31. A method for delivering agents to a defined biological space in vivo comprising:
providing a catheter comprising an outer catheter shaft defining at least one outer shaft lumen and having an outer shaft distal tip, and having an inner catheter shaft defining at least one inner shaft lumen and having an inner shaft distal tip, said inner catheter shaft disposed within and movable with respect said outer catheter shaft and disposing at least one deployable support member non-detachable positioned on at least one of said inner catheter shaft and said outer catheter shaft;
guiding said catheter to a surface of the biological space in vivo;
piercing a surface membrane of the biological space with said inner catheter distal tip;
deploying said at least one deployable support member;
infusing an agent into the biological space;
retracting said at least one deployable support member; and
withdrawing said catheter from said biological space.

32. The method of claim 31, wherein said deployable support member comprises at least one inflatable balloon in communication with at least one of said lumens of said inner catheter shaft or said outer catheter shaft.

33. The method of claim 32, wherein said deployable support member comprises at least one inflatable balloon positioned on said inner catheter shaft and in communication with at least one inner shaft lumen.

34. The method of claim 32, wherein said deployable support member comprises at least one inflatable balloon positioned on said outer catheter shaft and in communication with at least one outer shaft lumen.

35. The method of claim 32, wherein said deployable support member comprises at least one inflatable balloon positioned on said inner catheter shaft and in communication with at least one inner shaft lumen and at least one inflatable balloon positioned on said outer catheter shaft and in communication with at least one outer shaft lumen.

36. The method of claim 31, wherein said deployable support member comprises at least one deployable wire support in communication with at least one of said lumens of said inner shaft or said outer shaft.

37. The method of claim 36, wherein said deployable support member comprises at least one deployable wire support disposed on and in communication with at least one inner shaft lumen.

38. The method of claim 36, wherein said deployable support member comprises at least one deployable wire support disposed on and in communication with at least one outer shaft lumen.

39. The method of claim 36, wherein said deployable support member comprises at least one deployable wire support disposed on and in communication with at least one inner shaft lumen, and at least one deployable support member comprises at least one deployable wire support disposed on and in communication with at least one outer shaft lumen.

40. The method of claim 31, wherein the biological space is the pericardial space.

41. The method of claim 31, wherein the biological agent is a therapeutic agent.

42. The method of claim 31, wherein the biological agent is an angiogenic agent.

43. The method of claim 31, further comprising inflating at least one inflatable sealing balloon in communication with at least one of said lumens of said inner catheter shaft or said outer catheter shaft.

44. The method of claim 43, further comprising inflating at least one inflatable balloon positioned on said inner catheter shaft.

45. The method of claim 43, further comprising inflating at least one inflatable balloon positioned on said outer catheter shaft.

46. The method of claim 43, further comprising inflating at least one inflatable balloon positioned on said inner catheter shaft and at least one inflatable balloon positioned on said outer catheter shaft and in communication with said at least one outer shaft lumen, thereby providing a supported and isolated infusion of an agent into a biological space.

47. The method of claim 43, further comprising inflating a deployable support member comprising at least one inflatable balloon in communication with at least one said outer shaft and having said at least one inflatable sealing balloon disposed on said outer shaft and in communication with said at least one outer shaft lumen, thereby providing a supported and isolated infusion of an agent into a biological space.

48. The method of claim 43, further comprising inflating said at least one deployable support member comprising at least one inflatable balloon in communication with at least one said inner shaft and having said at least one inflatable sealing balloon disposed on said inner shaft and in communication with said at least one inner shaft lumen, and disposing said at least one deployable support member comprising at least one inflatable balloon in communication with at least one said outer shaft and having said at least one inflatable sealing balloon disposed on said outer shaft and in communication with said at least one outer shaft lumen, thereby providing a supported and isolated infusion of an agent into a biological space.

49. The method of claim 43, further comprising inflating said at least one deployable support member comprising at least one inflatable balloon in communication with at least one said inner shaft and having said at least one inflatable sealing balloon disposed on said outer shaft and in communication with at least one outer shaft lumen, and disposing said at least one deployable support member comprising at least one inflatable balloon in communication with at least one said outer shaft and having said at least one inflatable sealing balloon disposed on said outer shaft and in communication with said at least one outer shaft lumen, thereby providing a supported and isolated infusion of an agent into a biological space.

50. The method of claim 43, further comprising deploying a deployable support member comprising at least one deployable wire support in communication with at least one said inner shaft and having said at least one inflatable sealing balloon disposed on said inner shaft and in communication with said at least one inner shaft lumen, thereby providing a supported and isolated infusion of an agent into a biological space.

51. The method of claim 43, further comprising deploying a deployable support member comprising at least one deployable wire support in communication with at least one said outer shaft and having said at least one inflatable sealing balloon disposed on said inner shaft and in communication with said at least one inner shaft lumen, thereby providing a supported and isolated infusion of an agent into a biological space.

52. The method of claim 43, further comprising deploying a deployable support member comprising at least one deployable wire support in communication with at least one said inner shaft and having said at least one inflatable sealing balloon disposed on said outer shaft and in communication with said at least one outer shaft lumen, thereby providing a supported and isolated infusion of an agent into a biological space.

53. The method of claim 43, further comprising deploying a deployable support member comprising at least one deployable wire support in communication with at least one said outer shaft and having said at least one inflatable sealing balloon disposed on said outer shaft and in communication with said at least one outer shaft lumen, thereby providing a supported and isolated infusion of an agent into a biological space.

54. The method of claim 43, further comprising deploying said at least one deployable support member comprising at least one deployable wire support in communication with at least one said inner shaft and having said at least one inflatable sealing balloon disposed on said inner shaft and in communication with said at least one inner shaft lumen, and disposing said at least one deployable support member comprising at least one deployable wire support in communication with at least one said outer shaft and having said at least one inflatable sealing balloon disposed on said outer shaft and in communication with said at least one outer shaft lumen, thereby providing a supported and isolated infusion of an agent into a biological space.

55. The method of claim 43, further comprising:
   deploying positioned on said inner catheter shaft; and
   inflating at least one inflatable sealing balloon positioned on said outer catheter shaft.

56. The method of claim 31, wherein said catheter further comprises a proximal pusher portion and a distal end portion and said proximal portion is retractable from said distal end portion to uncover said inner catheter shaft.

* * * * *